United States Patent [19]

Asrar

[11] Patent Number: 5,200,470
[45] Date of Patent: Apr. 6, 1993

[54] NORBORNENE DICARBOXY PHENYLIMIDE POLYMERS

[75] Inventor: Jawed Asrar, Chesterfield, Mo.

[73] Assignee: Monsanto Company, St. Louis, Mo.

[21] Appl. No.: 809,987

[22] Filed: Dec. 18, 1991

Related U.S. Application Data

[63] Continuation-in-part of Ser. No. 629,910, Dec. 19, 1990, Pat. No. 5,115,037.

[51] Int. Cl.⁵ .............................................. C08F 8/04
[52] U.S. Cl. ................................ 525/326.8; 525/338; 525/339; 525/356; 526/259
[58] Field of Search ...................... 525/326.8; 526/259

[56] References Cited

U.S. PATENT DOCUMENTS 4,965,330 10/1990 Asrar .................................. 526/259

Primary Examiner—Bernard Lipman
Attorney, Agent, or Firm—Thomas E. Kelley; Richard H. Shear

[57] ABSTRACT

High Tg polymers prepared by metathesis ring-opening polymerization of N-aryl norbornene dicarboximide and one or more other norbornene derivative monomers, wherein said N-aryl group is substituted with a halo, cyano, alkyl or halogenated alkyl substituting group which is ortho or meta to the imide nitrogen. Preferred polymers with exceptionally high Tg are prepared from N-ortho substituted phenyl norbornene dicarboximide monomer. Mixtures of N-ortho substituted phenyl norbornene dicarboximide and N-meta substituted phenyl norbornene dicarboximide can exhibit eutectic melting points which facilitates melt polymerization.

6 Claims, No Drawings

NORBORNENE DICARBOXY PHENYLIMIDE POLYMERS

This application is a continuation in part of Ser. No. 07/629,910 filed Dec. 19, 1990, now U.S. Pat. No. 5,115,037, incorporated herein by reference, and discloses polymers derived from substituted phenyl imides of norbornene dicarboxylic acid, especially N-ortho substituted phenyl norbornene dicarboximide monomers; such polymers have desirable high temperature properties and are advantageously prepared by melt polymerization.

BACKGROUND OF THE INVENTION

U.S. Pat. No. 4,965,330 discloses that N-phenyl norbornene dicarboximides can be incorporated by metathesis ring-opening polymerization into polymers and copolymers having high glass transition temperatures (Tg). For instance, poly(N-phenyl)cyclopentyldicarboximide vinylene, a homopolymer prepared from N-phenyl norbornene dicarboximide, exhibits a Tg of about 225° C. Poly(N-p-chlorophenyl)cyclopentyldicarboximide vinylene, a homopolymer prepared from N-p-chlorophenyl norbornene dicarboximide, exhibits a Tg of about 230° C. And, poly(N-pcyanophenyl)cyclopentyldicarboximide vinylene-co-(N-phenyl)cyclopentyldicarboximide vinylene, a copolymer prepared from N-p-chlorophenyl norbornene dicarboximide and N-phenyl norbornene dicarboximide, exhibits a Tg of about 246° C.

Although N-aryl norbornene dicarboximide monomers can exist in both an endo and exo stereoisomeric form, the endo stereoisomer is not especially reactive in the formation of polymers. For instance, a low yield of a low molecular weight polymer is the typically result of polymerizing an endo stereoisomer of an N-aryl norbornene dicarboximide monomer. Exo stereoisomers of N-aryl norbornene dicarboximide monomers are more adapted to polymerization to high yields of high molecular weight polymers. The less reactive endo stereoisomers of N-aryl norbornene dicarboximide monomers have relatively lower melting temperatures than the exo stereoisomers, allowing for methods of separating the isomers, e.g. by melt crystallization. Because exo stereoisomers of N-aryl norbornene dicarboximide monomers typically have melt temperatures greater than 200° C., polymerization is most typically effected in solutions. For instance, U.S. Pat. No. 4,965,330 reports that the exo stereoisomeric form of N-phenyl norbornene dicarboximide has a melting point of about 200° and the exo stereoisomeric form of N-p-cyanophenyl norbornene dicarboximide has a melting point of about 228°. Melt polymerization is difficult because the high temperatures typically required to melt aryl norbornene dicarboximide monomers can be detrimental to the resulting polymer.

SUMMARY OF THE INVENTION

It has been discovered that ortho substituted phenyl imides of norbornene dicarboxylic acid can be polymerized to provide polymers having a substantially higher Tg than polymers prepared from other phenyl imides, e.g. unsubstituted phenyl imides or meta and para substituted phenyl imides. Thus, one aspect of this invention provides high heat performance polymers and copolymers prepared from N-ortho substituted phenyl norbornene dicarboximides. Another aspect of this invention provides novel and especially useful monomers of ortho or meta substituted phenyl imides of norbornene dicarboxylic acids.

It has also been discovered that mixtures of the ortho and meta substituted phenyl imides can form eutectic mixtures having sufficiently low melting points that allow for advantageously effective melt polymerization of aryl norbornene dicarboximides. Thus, another aspect of this invention provides copolymers prepared from mixtures of N-ortho substituted phenyl norbornene dicarboximide and N-meta substituted phenyl norbornene dicarboximide. Still another aspect of this invention provides methods of preparing polymers of N-aryl norbornene dicarboximide monomers comprising mixing a metathesis ring-opening polymerization catalyst in a molten mixture of N-ortho substituted phenyl norbornene dicarboximide and N-meta substituted phenyl norbornene dicarboximide, preferably where the mixture is selected so as to have a eutectic melting point as compared to the melting points of the ortho and meta substituted monomers.

DETAILED DESCRIPTION OF PREFERRED EMBODIMENTS

The N-aryl norbornene dicarboximide-based polymers of this invention can be homopolymers or copolymers prepared by using well known metathesis ring-opening polymerization techniques, including melt polymerization and solution polymerization, i.e. where the monomer is dissolved in solvent such as toluene or dichloroethane. Conventional metathesis polymerization catalysts include tungsten hexachloride catalyst with aluminum alkyl accelerator or ruthenium chloride catalyst. Preferred catalyst systems are the nonpyrophoric catalysts, comprising ruthenium initiator and tungsten catalyst, disclosed by Hardiman in U.S. application Ser. No. 07/531,663, incorporated herein by reference.

The polymers of this invention are prepared by metathesis ring-opening polymerization of N-aryl norbornene dicarboximide and one or more other norbornene derivative monomers. N-aryl norbornene dicarboximide monomer used to prepare the polymers of this invention have phenyl imide groups which are substituted at the ortho or meta carbon position of the phenyl ring with respect to imide nitrogen. In one aspect of the invention preferred monomers, useful for providing polymers with especially high Tg's, are substituted at the ortho carbon position of the phenyl ring. In another aspect of the invention, preferred monomers, useful for melt polymerization processes, are mixtures of ortho substituted phenyl imides and meta substituted phenyl imides. Appropriate selection of the molar ratio of ortho and meta substituted N-phenyl norbornene dicarboximides can advantageously provide monomer mixtures having a eutectic melting point substantially lower than the melting point of either of the ortho or meta substituted monomers when used alone.

The ortho and meta substituted N-aryl norbornene dicarboximide monomers useful in this invention can comprise any of a wide variety of substituents, e.g. halo, cyano, alkyl or halogenated alkyl substituents. Preferred substituents include fluoro, chloro, bromo, iodo, cyano, methyl and trifluoromethyl groups.

Norbornene dicarboximide monomers are advantageously derived from monomers of norbornene dicarboxylic acids. Such monomers are readily prepared through Diels-Alder reaction of cyclopentadiene and maleic anhydride by methods that are well known, e.g. as disclosed in U.S. Pat. No. 4,022,954, incorporated herein by reference. In general the Diels-Alder reaction product of cyclopentadiene and maleic anhydride is the endo stereoisomer which is not as well adapted to the production of high molecular weight polymers by metathesis ring-opening polymerization as is the exo stereoisomer. This endo stereoisomer can be converted to a predominately exo stereoisomer by heating and recrystallization using well-known procedures such as disclosed by Castner et al. in *Journal of Molecular Catalysis* 15, (1982) 47–59. For instance, in the case of norbornene dicarboxylic anhydride heating at about 198° C. for about two hours provides a molten equilibrium mixture of about 45 percent endo stereoisomer and about 55 percent exo stereoisomer. Predominately exo stereoisomer of norbornene dicarboxylic anhydride can be recovered by selective crystallization from a solvent such as toluene. Through multiple recrystallizations substantially high levels of the exo stereoisomer can be recovered, e.g. at least about 85 percent or higher. The dicarboximides can be prepared by reacting a primary amine, e.g. ortho methyl aniline, with the norbornene dicarboxylic anhydride providing an amic acid which can be readily imidized. Although the reactivity of aniline substituted with electron withdrawing groups, e.g. bromine, is significantly reduced, reaction with anhydride can be facilitated by the use of an acid or base catalyst, e.g. p-toluene sulfonic acid or triethyl amine. For many applications, it is preferred that the polymers of this invention be prepared from an N-aryl norbornene dicarboximide that is substantially exo stereoisomeric.

Depending on desired properties copolymers of this invention can be prepared from monomer mixtures comprising other norbornene derivative monomers such as norbornene nitrile, norbornene dicarboxylic anhydride, dicyclopentadiene, and other norbornene dicarboximides, e.g. N-methyl norbornene dicarboximide, N-ethyl norbornene dicarboximide, N-propyl norbornene dicarboximide, N-butyl norbornene dicarboximide, N-trifluoroethyl norbornene dicarboximide, N-phenyl norbornene dicarboximide, N-trifluoromethylphenyl norbornene dicarboximide and N-cyclohexyl norbornene dicarboximide. Copolymers with norbornene nitrile have enhanced solvent resistance.

Depending on the mix of monomers, polymers of this invention can have high Tg. For instance, a polymer having a number average molecular weight (Mn) of 29,000, prepared from N-m-methylphenyl norbornene dicarboximide (m.p. 133° C.), had a Tg of about 206° C.; a polymer having a Mn of 80,000, prepared from N-o-methylphenyl norbornene dicarboximide (m.p. 155° C.), had a Tg of about 248° C.; and a polymer having a Mn of 63,000, prepared from a mixture of 40 mole percent ortho substituted monomer and 60 mole percent meta substituted monomer (eutectic m.p. 114° C.) had a Tg of 220° C. It has been observed that the Tg of polymers based on ortho substituted phenyl imides increases with the size of the substituent group. This observation coordinates well with a molecular model relationship between Tg and rotation of the phenyl group. It has also been observed that in the case of polymers based on meta substituted phenyl imides the Tg is lowered with increasing size of the substituent. Apparently bulky meta substituents do not impede rotation of the phenyl ring or increase interchain free volume.

The polymers of this invention are useful as engineering thermoplastics for high temperature applications. The disclosure in the following examples illustrate specific embodiments and aspects of this invention but is not intended to imply any limitation of the scope of this invention.

EXAMPLE 1

This example illustrates a method for preparing polymers of N-aryl norbornene dicarboximide.

2 g of substantially exo-stereoisomeric N-ortho methylphenyl norbornene dicarboximide, melting point of 150°–155° C., was dissolved in 4 ml of 1,2-dichloroethane at 60° C. The solution was mixed with 0.1 ml of a catalyst solution comprising 0.5M tungsten hexachloride in toluene and 0.17 ml of an activator solution comprising 2M diethyl aluminum chloride in heptane. After mixing for about 2 hours the polymerization reaction was stopped by admixture of methanol. The recovered reaction product of poly(N-o-methylphenyl norbornene dicarboximide) had a Mn of 29,000 and Mw of 103,000 and a Tg of 248° C. (by DSC).

EXAMPLE 2

This example illustrates various methods for preparing polymers of this invention using the ortho and meta chlorophenyl imides of norbornene dicarboxylic acid (m.p. 174° C.). The solution polymerization procedure of example 1 was essentially repeated using the chlorophenyl imides. The polymer derived from the ortho chlorophenyl imide had a Tg of 255° C.; and the polymer derived from the meta chlorophenyl imide had a Tg of 204° C. The polymer prepared from the 50 mole percent mixture of the two monomers using solution polymerization had a Tg of 226° C.

EXAMPLE 3

This example illustrates the melt polymerization of a polymer according to this invention. The 50 mole percent mixture of the ortho and meta chlorophenyl imides used in Example 2 (eutectic m.p. 135° C.) was mixed with the tungsten hexachloride/aluminum alkyl catalyst system of Example 1 at a temperature of 140° C. After polymerization the reaction product was dissolved in methylene chloride and precipitated in methanol providing a polymer with a Tg of 208° C.

EXAMPLE 4

This example illustrates a variety of polymers according to this invention. Polymers were prepared using the methods of Example 1 from substituted phenyl imides of norbornene dicarboxylic acids as indicated in the following table. The Tg of such polymers is reported in comparison to the Tg of the polymer prepared from the unsubstituted phenyl imide.

| Imide Group | Polymer Tg |
| --- | --- |
| phenyl | 220° C. |
| o-methylphenyl | 248 |
| m-methylphenyl | 206 |
| 40/60 ortho/meta methylphenyl | 220 |
| o-fluorophenyl | 239 |
| m-fluorophenyl | 208 |
| 40/60 ortho/meta fluorophenyl | 219 |
| o-chlorophenyl | 260 |
| m-chlorophenyl | 204 |
| 40/60 ortho/meta chlorophenyl | 230 |
| o-bromophenyl | 270 |

| -continued | |
|---|---|
| Imide Group | Polymer Tg |
| m-bromophenyl | 200 |

While specific embodiments have been described herein, it should be apparent to those skilled in the art that various modifications thereof can be made without departing from the true spirit and scope of the invention. Accordingly, it is intended that the following claims cover all such modifications within the full inventive concept.

What is claimed is:

1. A polymer prepared by metathesis ring-opening polymerization of a eutectic-forming mixture of orthosubstituted and meta-substituted N-aryl norbornene dicarboximide monomers, wherein said N-aryl group is substituted with a halo, cyano, alkyl or halogenated alkyl substituting group.

2. A polymer according to claim 1 wherein said substituting group is fluoro, chloro, bromo, iodo, cyano, methyl or trifluoromethyl.

3. A polymer according to claim 2 wherein said N-aryl norbornene dicarboximide is substantially exo stereoisomeric.

4. A method of preparing polymers of N-aryl norbornene dicarboximide monomers comprising mixing a metathesis ring-opening polymerization catalyst in a molten mixture of N-ortho substituted phenyl norbornene dicarboximide and N-meta substituted phenyl norbornene dicarboximide.

5. A method according to claim 4 wherein said mixture has a eutectic melting point as compared to the melting points of the ortho and meta substituted monomers.

6. A polymer prepared by metathesis ring-opening polymerization of substantially exo stereoisomeric N-aryl norbornene dicarboximide and one or more other norbornene derivative monomers, wherein said N-aryl group is substituted with a fluoro, chloro, bromo, iodo, cyano, methyl or trifluoromethyl substituting group which is ortho or meta to the imide nitrogen.

* * * * *